(12) United States Patent
Hed et al.

(10) Patent No.: US 6,348,218 B1
(45) Date of Patent: Feb. 19, 2002

(54) SELF DOSING SKIN PREPARATION

(75) Inventors: Aharon Ze'ev Hed, Nashua, NH (US); Richard Pavelle, Winchester, MA (US); Sol Aisenberg, Natick, MA (US); George Freedman, Wayland, MA (US)

(73) Assignee: Invent Resources, Inc., Winchester, MA (US)

( * ) Notice: Subject to any disclaimer, the term of this patent is extended or adjusted under 35 U.S.C. 154(b) by 0 days.

(21) Appl. No.: 09/411,085

(22) Filed: Oct. 4, 1999

(51) Int. Cl.$^7$ ................................................ A61K 9/50
(52) U.S. Cl. ..................... 424/489; 424/401; 424/59; 424/63; 424/65; 424/69; 424/70.1
(58) Field of Search ................................ 424/401, 489, 424/63, 65, 59, 69, 70.1

(56) References Cited

U.S. PATENT DOCUMENTS 5,089,269 A  2/1992  Noda et al. .................. 424/456

*Primary Examiner*—S. Mark Clardy
*Assistant Examiner*—Michael A. Williamson
(74) *Attorney, Agent, or Firm*—Colucci & Umans; Peter C. Michalos; Angelo Notaro

(57) ABSTRACT

A self dosing skin composition and method releases sun blocking agent or other active ingredient onto the skin of a user as a function of exposure to at least one environmental condition over time. The environmental condition is preferably exposure to sun light, in particular, harmful UV radiation. The composition includes a medium adapted to be spread onto the skin of a user and a reservoir defining at least one wall for containing at least one sun blocking or other agent. The reservoir is dispersed in the medium and the wall is designed and/or selected to deteriorate over time with exposure to the environmental condition or conditions, for releasing the agent into the medium and onto the skin. At least one agent is provided in the reservoir. The reservoir is preferably in the form of a multiplicity of microcapsules dispersed in the medium, each microcapsule having a wall containing the at least one agent, each wall deteriorating over time with exposure to the at least one environmental condition for opening the microcapsule to release the agent.

41 Claims, 3 Drawing Sheets

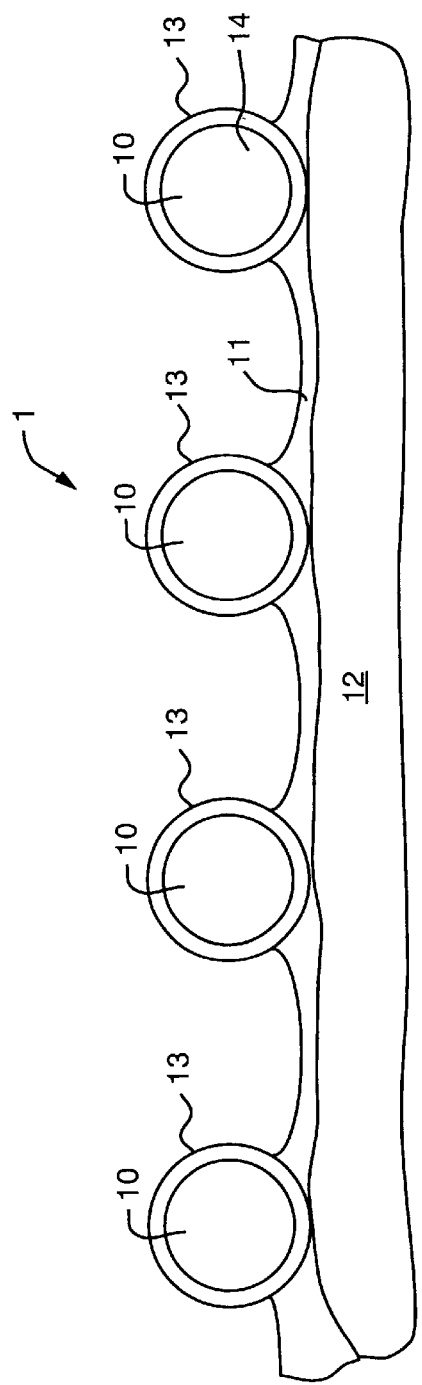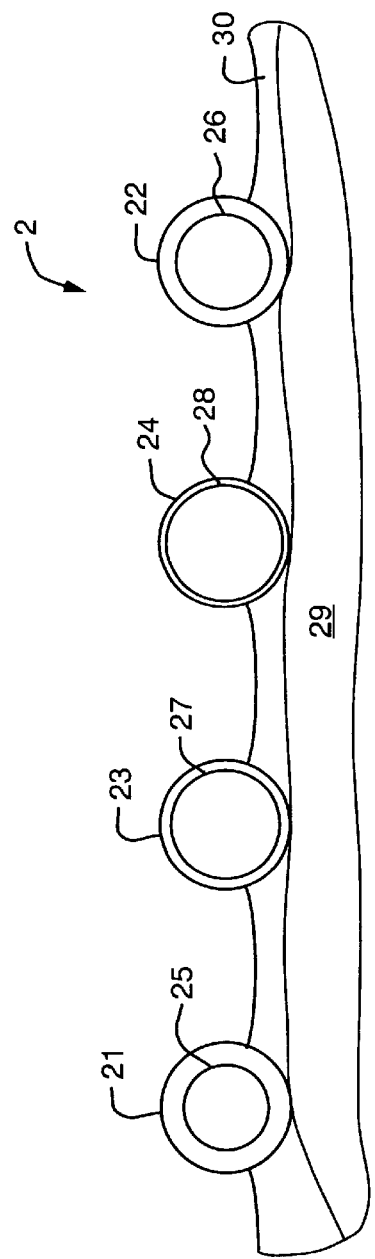

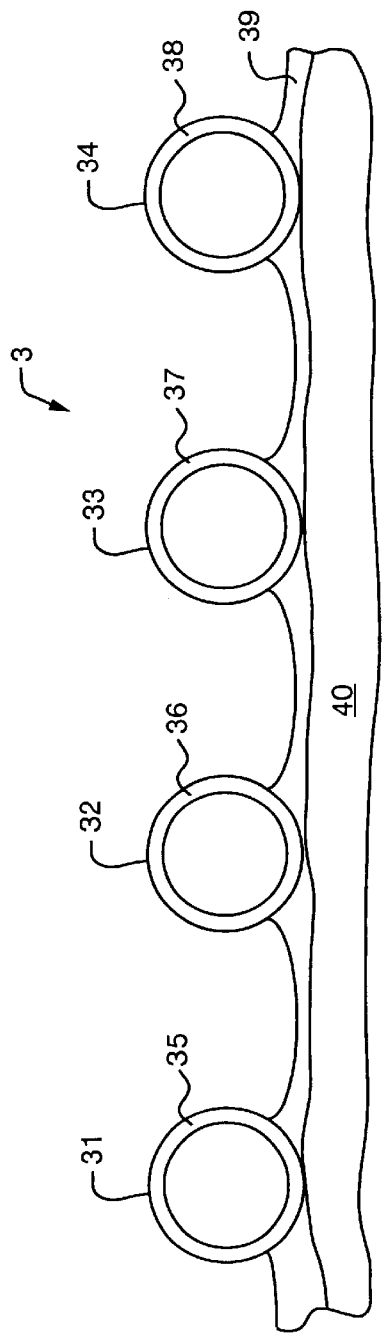
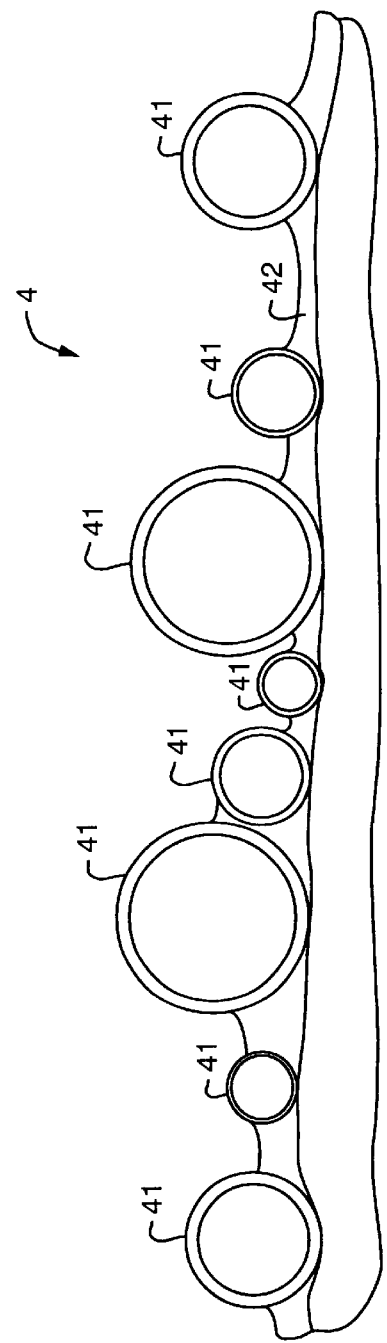

SELF DOSING SKIN PREPARATION

FIELD BACKGROUND OF THE INVENTION

This invention relates, in general, to skin preparations, and in particular to a new and useful self dosing preparation which releases one or more active ingredients onto the skin after exposure to the sun or other environmental condition. The active ingredient may include a sunscreen having a UV absorption effect or another skin preparation that is maintained or which increases with exposure to solar radiation. The invention is also generally concerned with creams or lotions containing these preparations as well as various cosmetic compositions containing self dosing sunscreens and/or other skin preparations containing self dosing ingredients such as, but not limited to, fragrances, antiperspirants, dyes, cooling/warming agents, flavors, insect repellents, antibacterial agents, hair conditioners and self tanning agents.

Erythema or "sunburn" is the direct consequence of exposure of the skin to solar or sun radiation, and particularly the part of the spectrum in the range of 280 to 320 nanometers or UVB, also known as the erythematosus part of the solar spectrum. Furthermore, this part of the spectrum has sufficient energy per photon (between 3.8 to 4.4 electron volts) to cause ionization of organic molecules, including DNA, and is thus considered to be mutagenic, and thus, it is believed that exposure to UVB is a major causal contributor to basal cell carcinoma.

Over the years there have been a number of compounds identified and developed for incorporation in suntan lotions that absorb in the range of 280 to 320 nanometers. Such compounds also require, however, additional properties. It is desired that they transmit some of the solar radiation in the 320 to 400 nanometers range (UVA) in order to enhance tanning. These compounds also must be compatible with carriers and other ingredients in suntan lotions and creams as well as in other cosmetic preparations, such as, but not limited to, base creams, lipsticks and make up preparations. Such compounds also must be non-odorous and be nontoxic and dermatologically compatible.

One can divide topical UV blocking compounds into essentially two classes, organic compounds and inorganic compounds.

Typically, inorganic compound based sunscreens and suntan lotions are formulated within creams and lotions and include fine dispersion of a number of inorganic minerals like kaolin and chalk, or oxides such as titanium dioxide and zinc oxide. These inorganic sun screens have a number of aesthetic as well as health problems related with their use. When applied, they form a white layer which is objectionable to most users. Furthermore, the fine particles of these inorganic materials have a tendency to be lodged in hair follicles resulting in inflammation. Cases of sweat gland inflammation due to occlusion have been reported as well. Furthermore, these inorganic based sunscreens re-liquify when mixed with the wearer's perspiration and have a tendency to soil the wearer's garments and are thus objectionable for that reason as well.

Mitchnick et al. in U.S. Pat. No. 5,733,531 suggest to remedy these problems by encapsulating the oxides or pigments into spherical microcapsules having a diameter as large as 100 microns and as small as 0.01 micron. However, it is quite clear that in such an arrangement, when the particles are on the "high side" of the proposed dimensions (at or near 100 microns) in interstitial light diffusion will cause UVB to reach the epidermis, and in the lower end of the proposed range, the entire microsphere will have a tendency to lodge itself into hair follicles and sweat glands as do the traditional inorganic sunscreen agents. Furthermore, large microcapsules will have a tendency to break and discharge their content (sub-micron sized inorganic oxides) resulting in the same problems cited above.

Representative organic compounds that have been found to possess desired UVB blocking or absorption properties, are typically aromatic compounds, such as derivatives of para-aminobenzoic acid (PABA), PABA esters (glyveryl PABA), amyldimethyl PABA, octyldimethyl PABA and 2-ethylhexyl-paradiethylamino benzoate. These are just a few of the many examples of the PABA type active ingredients in suntan lotions. Benzophenones (Escalol 567), oxybenzone such as 2-hydroxy-4-methoxy benzophenone as well as sulisobenzone, have been used as active ingredients in sunscreen preparations as well. Cinnamates, such as octyl-methoxy-cinnamate (also known as Escalol 557 or Parsol MCX or cinoxate) are also used in this fashion. Salicylates such as homomethyl salicylate have also been used as well as anthranilates such as methyl anthranilate. These compounds are in no way exclusive and many other aromatic compounds have been used over the years as UV blocking agents in suntan lotions and other cosmetic preparations.

One of the shortcomings common to many of these organic UVB absorbing compounds is that relatively large concentrations of these blocking agents must be used to achieve the desired "Protection Index" or PI. The PI is defined as the ratio of the irradiation time required to reach the erythematogenic threshold with the UV screen divided by the irradiation time required to reach the erythematogenic threshold without the UV screen. Naturally, the higher the index, the better is the blocking action of the UV screening agent used. Another shortcoming of most of the existing compounds is believed to be rooted in the fact that the active agents in most sunscreens are relatively small molecules and in time, part of these are absorbed into the epidermis and lose some of their sun blocking action. This require that the user frequently reapply the sunscreen formula to exposed portions of the body, so as to avoid sunburns or erythema.

U.S. Pat. Nos. 3,980,617; 4,107,290 and 4,233,430 to Jacket et al. disclose attempts to overcome these problems by fixing the UV absorbing moieties on certain macromolecular polymers through an acrylamino group replacing hydrogen or other radicals on the main polymer carbon chain. This polymeric structure which has a dangling carbon-carbon bond, is itself subject to UV degradation, however.

Cosmetics and suntan lotions that contains microencapsulated ingredients, including UV blocking ingredients have been described before, for instance, by Noda et al. in U.S. Pat. No. 5,089,269. Neither this patent nor any of the prior art the inventors are aware of provide for microcapsules that act as a reservoir for releasing the active ingredient as a function of exposure to UV radiation, however.

There is therefore a need for sunscreen systems based on the traditional UVB absorbing aromatic compounds as well as newer compounds, which provide for long term protection, and actually has an increasing PI as a function of exposure to UVB, solar radiation or at least on environmental condition, in general.

Furthermore, there is a need to include such self dosing sun blocking agents in other cosmetic preparations such as make up, lipsticks, various creams and emollients. There is also a need for cosmetic preparations in which fragrances, dyes or antiperspirants are discharged as a function of exposure of the preparations to solar radiation and other environmental conditions.

SUMMARY OF THE INVENTION

The inventors have surprisingly found that encapsulating active ingredients for the skin, within capsules whereby the capsules' wall material deteriorates with exposure to the elements, and particularly to the UV part of the solar spectrum, provide a continuous mechanism for replenishing a film of UV absorbing agent or other active ingredients onto the skin.

A preferred embodiment of the invention includes a spectrum of capsules, differing in wall deterioration characteristics, so that some of the capsule walls deteriorate rapidly, while others deteriorate slowly so as to provide, with exposure to the elements and UV flux from the sun, a PI that increases with exposure, or in essence a "self dosing" sunscreen whereby the longer a person treated with the innovative sunscreen is in the sun, the higher the PI of the sunscreen, a feature heretofore not achieved in the prior art.

Accordingly, an object of the present invention is to provide means and methods resulting in sunscreens having a PI that increases with exposure to UV radiation in general.

It is another object of the present invention to provide a sunscreen in which the LTV absorbing agents are encapsulated in microcapsules having walls that are susceptible to UV degradation and subsequent release of the active ingredients.

It is another object of the present invention to provide a sunscreen in which the UV absorbing agents are encapsulated and the material of the encapsulating wall deteriorates with time due to natural degradation processes, such as exposure to humidity, oxygen in the air or light in general.

It is yet another object of the present invention to provide a sunscreen in which the active UV absorbing ingredients are encapsulated in microcapsules having walls that deteriorate with exposure to UV and other external natural agents at varying rates.

Accordingly a still further object of the invention is to provide a self dosing sunscreen composition and method for releasing sun blocking agent onto the skin of a user as a function of exposure to at least-one environmental condition over time. The environmental condition is preferably exposure to sun light, in particular, harmful UV radiation. The composition includes a medium adapted to be spread onto the skin of a user and a reservoir defining at least one wall for containing at least one sun blocking agent. The reservoir is dispersed in the medium and the wall is designed and/or selected to deteriorate over time with exposure to the environment condition or conditions, for releasing the sun blocking agent into the medium and onto the skin. At least one sun blocking agent is provided in the reservoir. The reservoir is preferably in the form of a multiplicity of microcapsules dispersed in the medium, each microcapsule having a wall and containing the at least one sun blocking agent, each wall deteriorating over time with exposure to the at least one environmental condition for opening the microcapsule to release the agent.

A still further object of the invention is to provide self dosing cosmetic or other preparations and compositions, and methods for releasing fragrances, antiperspirants, dyes, cooling/warming agents, flavors, insect repellents, antibacterial agents, hair conditioners, self tanning agents and/or other active ingredients onto the skin of the user, as a function of exposure to a least one environmental condition over time. The environmental condition is preferably exposure to sunlight. The composition includes a medium adapted to be spread onto the skin of a user, and a reservoir defining at least one wall for containing at least one fragrance or antiperspirant or cosmetic dye, or any other active ingredient. The reservoir is dispersed in the medium and the wall is designed and/or selected to deteriorate over time with exposure to the environmental condition or conditions, for releasing active ingredient or active agent into the medium and onto the skin. At least one ingredient or agent is provided in the reservoir. The reservoir is preferably in the form of a plurality of microcapsules dispersed in the medium, each microcapsule containing the at least one ingredient or agent and the walls of the microcapsules deteriorating over time with exposure to the at least one environmental condition, such deterioration resulting in the release of the ingredient or agent.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which embodiments of the invention are illustrated.

BRIEF DESCRIPTION OF THE DRAWINGS

In the drawings:

FIG. 1 is a side elevational view of a plurality of microcapsules containing UV screening agents homogeneously distributed within a carrier film of a cosmetic preparation;

FIG. 2 is a view similar to FIG. 1 of an embodiment of the invention in which the walls of the degradable microcapsules vary in thickness between the various capsules;

FIG. 3 is a view similar to FIG. 1 of an aggregation of microcapsules having walls differing in chemical constitution thus rendering some more and some less susceptible to degradation;

FIG. 4. a view similar to FIG. 1 of a sunscreen having microcapsules of various sizes;

DESCRIPTION OF THE PREFERRED EMBODIMENTS

Figure 5:
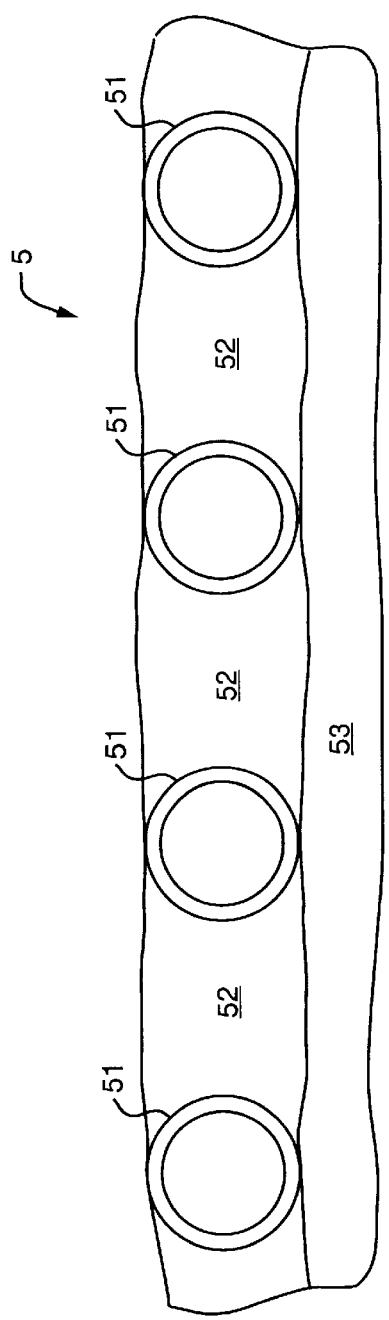
FIG. 5 a view similar to FIG. 1 of a higher viscosity carrier building a film that essentially contains the microcapsules.

To achieve the stated objects and other objects that will become apparent, a reservoir of UV blocking agent, or other cosmetic or non-cosmetic agents such as fragrances, antiperspirants or dyes, is provided, the reservoir slowly opening to discharge its contents in a controlled manner, to create a film containing the UV absorbing agents. The film includes a lotion or cosmetic preparation which thus spreads over the epidermis of the wearer. The controlled manner is such that the effective PI stays constant or actually increases with the exposure to sunlight.

While in the following description we will concentrate on UV blockers as the encapsulated active ingredient in various cosmetic preparations, it should be clearly understood that other active ingredients and agents such as fragrances, antiperspirants, dyes and other agents are contemplated as self dosed species of the inventions.

In a preferred embodiment of the invention, the active UV absorbing ingredient is present in the lotion at a relatively low concentration and the majority of the active ingredient is microencapsulated. The microcapsules have a wall material that degrades when exposed to UV. Upon degradation, the microcapsule ruptures or otherwise develop fissures or pinholes and releases its content, thus compensating for the loss of the active ingredient in the lotion over time.

In some embodiments of the invention, the size distribution of the microcapsules is relatively homogeneous as is the average thickness of the microcapsule walls and the degradation obeys an exponential decay law to assure sufficient protection for a selected period of time. The half-life time for degradation to "failure" (failure meaning the beginning of seepage of the microcapsule's content) is selected to be about 4 hours by appropriate selection of the thickness of the wall, or from about ½ to about 6 hours.

In some other embodiments of the invention, a spectrum of microcapsule walls is selected to offer a more constant rate of release as portions of the microcapsule population having thinner walls degrades first and discharge their content, followed by the degradation of progressively thicker walls to provide for a more linear discharge or even a discharging rate that actually increases with exposure to UV.

In yet another embodiment of the present invention, the population of microcapsules is designed to contain two or more microcapsules sizes providing for different time release constants which together result in homogeneous release of the active agents such as but not limited to, sunblockers, fragrances, antiperspirants, dyes, cooling/warming agents, flavors, insect repellents, antibacterial agents, hair conditioners and self tanning agents, into the lotion carrier.

In yet another embodiment of the present invention, the population of microcapsule contain microcapsule walls that have varying degrees of susceptibility to UV degradation, thus allowing for different half-lives of these populations and as a result a more homogeneous discharge rate into the lotion carrier.

In yet another embodiment of the invention, the microcapsules are hybrid capsules having an inner wall that is light sensitive and deteriorates with exposure, and an outer wall that is soluble in a portion of the carrier of the UV blocking agent contained within the microcapsule core. The outer walls of the capsules are further designed in such as way that the UV flux transmitted there through, to the inner wall, varies between different capsules thus providing for staggered release of the UV blocking agent and other cosmetic or non-cosmetic ingredients within the microcapsules into the lotion.

The present invention provides for a reservoir of cosmetic of other agents but particularly UV blocking agents that are discharged into the carrier of the lotion as a result of exposure of the lotion or cosmetic preparation to the elements, and particularly, to the UV part of the sun's radiation. While many such reservoirs can be contemplated, and are intended to be part of the method of providing for a UV dose dependence of the PI of various sunscreens, lotions and other cosmetic preparations, in the following description of the preferred embodiments, the said reservoir consists of an agglomeration of encapsulated UV blocking agents within microcapsules whose shells or walls, degrade to the point of rupture or fissure of the shell, or to the point of seepage of the encapsulated species through the degraded shell.

FIG. 1 is a schematic diagram illustrating a supply of composition or reservoir means 1, comprising an aggregate of microcapsules 10 embedded within a lotion, cream of other medium 11, which is smeared on the skin or epidermis of a user at 12. The microcapsules 10 have an outside wall or shell 13 with and an inner space or volume filled with a UV blocking agent 14.

The blocking agent 14 can be any of the commercially available UV or sun blocking agents or compounds that are well known in the prior art, including but not limited to:

benzophenones (Escalol 567-benzophenone, 2-hydroxy-4-methoxy benzophenone, and sulisobenzone);

PABA and PABA derivatives (paraaminobenzoic acid and PABA esters (glyveryl PABA), amyldimethyl PABA, octyldimethyl PABA, 2-ethylhexyl-para-diethylamino benzoate;

cinnamates (octyl methoxy cinnamate—also known as Escalol 557—another source for the same is Parsol MCX, or cinoxate);

salicylates (homomethyl salicylate);

aminobenzoic acid ester;

anthranilates (such as Methyl anthranilate);

2-ethylhexyl-2-cyano-,3-diphenyl acrylate;

2-phenyl benzimidazole-5-sulfonic acid;

aialloyl trioleate;

3-(4-methyl benzyledene) camphor;

4-isopropyl dibenzoyl methane;

butyl methoxy dibenzoyl methane;

2-ethyl-2-cyano-3,3'diphenyl acrylate;

1-naphtyl-N-methyl carbamate;

ascorbic acid;

N-(hydroxymethyl)-N-(1,3-dihydroxymethyl-2,5-dioxo-4-imidazolidinyl-N'-hydroxymethyl urea;

magnesium 1-hydroxy2(1H)-pyridinethione;

N-(4-chlorophenyl)-N'-(3,4-dichlorophenyl) urea; and/or

N-(1-chloro,2-methyl,3-beta-chloronaphtylether benzyl)-N'-chlorobenzoyl urea.

Most of these UV blocking agents are immiscible with water and thus are easily encapsulatable by standard coacervation methods. Few of these compounds are water soluble (such as ascorbic acid), and are pretreated to render them coacervationable in a water medium. For instance, when using ascorbic acid as the UV blocking agent, the ascorbic acid is first dispersed in a water insoluble agent such as petrolatum or dimethicone, then the dispersion is mixed and agitated in water to create a micro-droplet suspension and that is followed by in situ polymerization of the shells on the micro-droplets from an appropriate water soluble monomer using suitable free radical polymerization initiators.

One such group of water soluble monomers whose polymer degrades with exposure to UV radiation is vinylpyrrolidone as well as various alkyl-vinylpyrrolidones. A suitable initiator of the polymerization that can be used to affect shell formation in the coacervation process is t-butylperoxypivalate.

The coacervation process follows well known procedures in the prior art. In this case, the UV blocking agent or solutions thereof in lipophilic agents, is first dispersed in water. The droplet size is determined by the degree of agitation applied, the monomer of choice is added to the solution (about 10% by volume) and then the temperature is raised to about 80° C. and maintained there as the initiator is added, while the solution is slowly stirred (either magnetically or by propeller stirring). The longer the polymerization process is allowed to progress, the thicker the resulting microcapsule walls. For very thick walls, the inventors found that it is sometimes necessary to decant the excess solution, wash the microspheres and repeat the process with fresh vinylpyrrolidone or alkyl-vinylpyrrolidone.

In some embodiments of the reservoir described in FIG. 1 the actual final product is constituted from microcapsules of the same size and wall composition, but the content of the microcapsules is varied. Thus one third may contain one blocking agent from the list provided above, another third another agent and the final third, a third blocking agent. Any desired ratio of capsules containing differing blocking agents can be utilized as well. This admixing in a single carrier of a spectrum of blocking agents allows the design of a lotion or any cosmetic preparation having a broad spectrum of UV absorption, or even an absorption which is only selectively blocking. Thus in some lotions, one could have blocking of only the UVB part of the spectrum while in others both the UVB and the UVA parts of the spectrum are blocked. Any ratio of absorption can be designed in this fashion as well.

By the correct selection of encapsulated ingredients and the half-life to degradation of the microcapsule walls, one can essentially design a system that results in UV exposure dependent UV blocking agents in any part of the spectrum and any temporal sequence desired, as well.

When using a UV blocker reservoir as shown FIG. 1, where the microcapsule's size distribution is relatively homogeneous, approximate average capsule diameters in the 3 to 10 micron range are preferred. The carrier in the lotion or medium 11 can be any of a number of well known carriers and cosmetic preparations in the prior art as long as they do not act to dissolve the microcapsule walls during storage. One can include an agent that will, under the influence of light, and particularly UV light, act on the microcapsule walls to slowly dissolve the walls and thus gradually release the content of the microcapsules into the lotion 11. In some embodiments of the invention, film forming polymers are used in the carrier to enhance adhesion of the particles to the skin and prevent premature breakage. Such film forming polymers can be selected from the following well known substances:

hydroxyethyl cellulose;

hydroxypropyl cellulose;

hydroxyethyl alkali metal carboxyalkyl cellulose derivatives;

free acid hydroxyalkyl carboxyalkyl cellulose derivatives;

polyvinyl alcohol;

vinylpyrrolidone homopolymers and copolymers;

polycarboxylic acid derivatives;

polyacrylamides;

vinyl ethyl ether homopolymers and copolymers; and/or ethylene oxide resins.

Similarly, in order to maintain the microcapsules in suspension, emulsifiers can also be included in the lotion, 11. Such emulsifiers can be for instance polyoxyethylene, lauryl ether (Brij 35-ICI Americas) and glyceryl mono-dioleate (Capmul GMO—Karlshammus, USA).

The carrier 11 can of course include additional ingredients such as emollients, moisturizers as well as perfume concentrates, depending on the nature of the lotion, the cream of the cosmetic preparation desired.

In operation, the lotion or cosmetic preparation is rubbed onto the skin, and a small fraction of the microcapsules break and release into the carrier its UV blocking agent or other active cosmetic agents and ingredients. In some embodiments, the carrier itself is partially loaded with the UV blocking agent as well. The initial concentration in the carrier together with the rubbing induced minor rupture of capsules provide for the initial desired protection index. As the sunlight acts on the encapsulated species, the wall starts to degrade and the capsule ruptures or develop fissures, allowing discharge of the capsules' content.

The mechanism of UV or environmental capsule degradation, while not fully elucidated at this time, is of little importance since the result is still the release of the active UV blocking agent, from the reservoir, or the aggregate of the microcapsules, into the carrier. The inventors believe that in some cases, UV induced crazing of the shells provide sufficient fissures to allow seepage of the microcapsules' content. The fissures could be the result of UV induced bond breaking in the shells polymer, or inducement of a more brittle state of the polymer. There is also a possibility that hydrostatic pressure develops within the capsules, since in essence each capsule serves as a mini lens that could concentrate the sunlight's flux (in the whole spectrum and not only the UV part) causing slight overheating of the material within the capsule and thus causing capsule breakage.

Regardless of the mechanism, according to the invention the reservoir means that defines the wall for containing the sun blocking agent, that is the microcapsules in the preferred embodiments of the invention, must have a wall that deteriorates over time with exposure to at least environmental condition for releasing the agent into the medium and onto the skin. The word "deteriorates" is meant to include any of the above-identified mechanisms or any other mechanisms that open the wall or otherwise result in discharge of the contents of the microcapsule. Although the preferred environmental condition is UV exposure, the wall may be selected to deteriorate over time when exposed to any other environmental condition.

FIG. 2 schematically illustrates a reservoir 2 of UV blocking agents encapsulated within microcapsules having wall thickness differences. In essence, the aggregate of microcapsules is assembled from microcapsules made through different processes of coacervation. Thus the class of microcapsules 21 may have the thickest wall 25 and the wall thicknesses 26, 27 and 28 in capsules 22, 23 and 24 respectively, decreases progressively.

In operation, the lotion or carrier 30 is applied on the skin 29 and as before a small fraction of the microcapsules fracture during that process, to provide an initial PI, which can be further raised, as mentioned above by adding in the carrier solution a certain initial amount of the UV blocking agent selected for that purpose.

This arrangement allows for fractions having half-life times ranging from as little as about ½ hour (in full sun), for the thinnest wall microcapsules to as much as about six hours for the thickest microcapsules. By selecting the ratio of the different fractions appropriately, one can design a sunscreen having a PI which actually increases with exposure to the sun, or, on the other hand, a sunscreen having a PI that stays relatively constant throughout the exposure to the sun.

While in FIG. 2, the external diameter of the microcapsules is shown to remain constant, even though, the wall thicknesses vary between the various fractions of microcapsules, and thus the content of the microcapsule decreases somewhat as the wall thickness increases. It should be understood that the thickness differences between the various microcapsules depicted in this figure is much greater than in practice. These differences were amplified in the figure only for visual demonstration of the concept. It should also be clear that one can design a system in which the various fractions have relatively the same volume of active agents in all the microcapsules, independently of the thickness of the microcapsules walls.

FIG. 3 shows yet another embodiment of the methods of controlling UV absorption by using a lotion as a function of its total UV dose, with a reservoir 3 comprising a plurality of microcapsule aggregates, each aggregate having microcapsules 31, 32, 33 and 34 respectively. Within each aggregate the size of the microcapsules are more or less the same, however the chemical compositions of the walls, 35, 36, 37 and 38 of the microcapsules 31, 32, 33 and 34 respectively, is changed to monotonically increase their susceptibility to UV dosage and thus one obtains a reservoir 3 that discharges to the lotion 39 the UV blocking agent enclosed within the said capsules in a sequential manner and in response to UV radiation impinging on the lotion.

One method of obtaining variability of wall susceptibility to degradation is by using as monomers, vinylpyrrolidone in conjunction with alkyl-vinylpyrrolidone, and obtaining more UV susceptible shells the greater the concentration of the alkyl-vinylpyrrolidone. Appropriate alkyl-vinyl pyrrolidone for that purpose can be any of methyl-vinylpyrrolidone, ethyl-vinylpyrrolidone and butyl-vinylpyrrolidone. Initiators for the polymerization reaction can be the same as described above for vinyl pyrrolidone in situ polymerization.

In operation, as before, rubbing the lotion 39 over the skin 40 will cause a minority of the microcapsules to rupture and provide an initial dose of UV blocking agents in the lotion. With initial exposure to UV, degradation of the most alkylated polyvinylpyrrolidone shells occurs, and that causes release of UV blocking agents encapsulated therein, and with additional exposure, microcapsules having walls made of less alkylated polyvinylpyrrolidone will rupture followed by capsule made of almost exclusively non alkylated polyvinylpyrrolidone, thus providing a method and a reservoir to discharge the UV blocking agent as function of the UV dose experienced by the wearer of said lotion.

FIG. 4 illustrates yet another embodiment of the self dosing UV sunscreen of the present invention. In this case the reservoir 4 consists of a plurality of microcapsules 41 having a broad range of diameters (from about 3 to 50 microns), all the microcapsules have a UV degradable shell, as described above, and the wall thickness and chemical compositions of said microcapsules' walls are essentially the same. Surprisingly the inventors have found that the larger the diameter of the capsules. (in the range of 3 to 50 microns), the faster the rate of capsule rupture under the influence of UV flux. While this phenomenon has not been fully elucidated, the inventors believe that it might be related to partial immersion of smaller capsules within the lotion, said immersion involving a much greater proportion of the surface of smaller microcapsules than the larger microcapsules. It is also possible that the larger microcapsules are intrinsically more fragile and thus a smaller degree of UV degradation cause rupture than in smaller microcapsules. In any event, when using about 10% of the larger microcapsules (30 to 50 microns), about 20% of medium microcapsules (10 to 30 microns) and about 70% of the smaller microcapsules, a relatively constant rate of discharge of the microcapsules' content over a period of about six hours exposure to UV occurs. Thus providing for a reservoir that discharges its UV blocking agent in response to UV dosage relatively homogeneously.

A cosmetic preparation, cream or suntan lotion having within it encapsulating active ingredients can be designed that includes the combination of a number of the principles and methods described herein, thus capsules having different sizes, wall thickness and walls UV susceptibility variations can be combined to provide for a desired predetermined rate of release as function of integrated UV exposure of the preparation on the wearer of such products.

In some embodiments of the invention, when it is desired to slow down the discharge of the UV blocking agent from the reservoir of microcapsules, the carrier or lotion is "thickened" to provide it with higher viscosity and thus thicker films of the carrier are applied which fully cover the microcapsules therein. Such a reservoir 5 is shown in FIG. 5, whereby the microcapsules aggregate 51 is fully embedded in the carrier 52 when applied over the skin or epidermis 53.

Appropriate thickening agents that can be used in the carrier 52 include, but are not limited to, hydroxypropyl cellulose, sodium carboxymethylcellulose, xanthan gum, hydroxyalkyl cellulose as well as alkyl cellulose.

Figure 6:
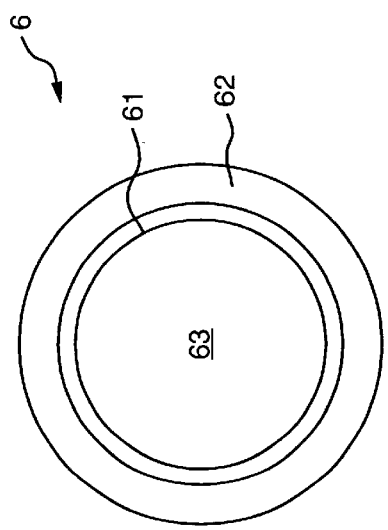
FIG. 6 a view similar to FIG. 1 of an embodiment of the invention in which the microcapsules possess a double wall and the failure of the capsule wall and thus the discharge of the microcapsules' content is triggered by a reaction in the inner wall followed by partial dissolution of the outer wall, in contact with specific agents in the UV absorbing species in the cores of the microcapsules.

In yet another embodiment of the invention, the microcapsules constituting the UV blocking agent reservoir are hybrid capsules, an example of which is shown in FIG. 6. In this embodiment, the microcapsule 6 has two concentric walls, 61 and 62, enclosing the active UV blocking ingredient 63. The inner wall is made to include a photosensitive agent that causes the inner wall to deteriorate with exposure to either light in general, or specifically to UV exposure. The inner core 63, contains both one or more UV blocking agents as well as a solvent capable of dissolving the outer shell 62 but not the inner shell 61. When the inner wall is exposed to ambient light or the UV part of the sun's spectrum, fissures develop in said inner wall of the microcapsules allowing some of the solvent to dissolve the outer wall, 62 and in that manner releasing the UV blocking agent within the core, 63, into the lotion.

The aggregation of microcapsules 6 in the reservoir consists of a mixture of microcapsules having varying thickness of the external wall, 62. Due to Baer law, the flux of activating light, reaching the light or UV sensitive inner wall, 61, will thus decrease exponentially with the thickness of the external wall 62. Thus microcapsules, 6 having a thin external wall 62 will degrade very rapidly, while microcapsules having a thicker external wall, 62, will degrade at a much slower rate. In that manner the reservoir of UV blocking agent is controllably discharged into the lotion and provide a UV dose dependent concentration of the UV blocking agent within the lotion.

In this embodiment of the invention, the inner core can contain, for instance a mixture of para-amino-benzoic acid (PABA) with dimethicone, the inner wall 61 be made mostly of butyl-vinyl pyrrolidone and methyl vinylpyrrolidone, and the external wall 62 for instance from lipids or protein derivatives and gelatin.

While the inventors have concentrated on the preferred embodiments of the invention including the controlled discharge of UV blockers from a reservoir of microcapsules having walls susceptible to UV degradation, the same principles can be applied to any encapsulated substance within said microcapsules, such as but not limited to, antiperspirants, cosmetic dyes, cooling agents, a warming agents, flavors, insect repellents, antibacterial agents, hair conditioners, self tanning agents and/or fragrances, where it is desired to cause discharge of the microcapsules' content as a result of the cumulative influence of light in general and UV flux in particular.

Examples of skin compatible dyes that can be encapsulated and used in the present invention are: D&C Yellow No. 11; D&C Violet 2; D&C Green 6; D&C Red 17; and combinations thereof.

Examples of skin compatible cooling agents that can be encapsulated and used in the present invention are: wintergreen oil; menthol crystals dissolved in oil; peppermint oil; camphor; and combinations thereof. Examples of skin compatible warming agents that can be encapsulated and used in the present invention are: capsaicin and nicotinamide.

Examples of skin compatible flavors that can be encapsulated and used in the present invention are oil extracts from fruits such as raspberry oil, pear oil and banana oil or fragrance compounds that provide a flavor of raspberry, banana, etc.

DEET (N,N-diethyl-3-methylbenzamide and citronella are examples of insect repellents, triclosan is an example of an antibacterial agent and silicone oil is an example of a hair conditioner that can be used as the active ingredient of the present invention. The encapsulated agent may also be a hair lightener such as peroxide of other hydrogen peroxide composition. Hair coloring may also be encapsulated according to the invention, e.g. coloring derived from a plant source such as chamomile, black walnut, hibiscus, marigold, indigo, blue malva, logwood and henna. Self tanning agents include dihydroxyacetone (DHA).

Having described certain preferred embodiments of the present invention, including the methods of providing for a reservoir of active ingredient releasing its content as function of the amount of UV flux exposure, and various cosmetic products incorporating such reservoirs, many modifications will occur to those skilled in the art, including active ingredients that are not necessarily UV blocking agents. It is therefore desired that it be understood that it is intended herein to cover all such modifications that fall within the spirit and scope of this invention.

While specific embodiments of the invention have been shown and described in detail to illustrate the application of the principles of the invention, it will be understood that the invention may be embodied otherwise without departing from is such principles.

What is claimed is:

1. A cosmetic composition for releasing an active agent onto a user's skin at a release rate, the release rate being a function of exposure to UV radiation, the composition comprising:

a medium adapted to be spread onto the user's skin;

a multiplicity of microcapsules dispersed in said medium, said microcapsules containing at least one active agent, and said microcapsules having sufficient strength so that only a minority of the microcapsules rupture during application of the composition onto the user's skin;

said release rate being controlled by providing a population of microcapsules with half-life times to deterioration under the influence of the UV radiation which is about ½ hour to about 6 hours.

2. A composition according to claim 1, wherein the half life time of said microcapsules to deterioration under UV radiation is controlled by one or more of the following parameters: microcapsule wall composition; microcapsule wall thickness and microcapsule diameter; and said sufficient strength is achieved by said microcapsules each having a diameter not greater than 50 microns.

3. A composition according to claim 2, wherein said multiplicity of microcapsules contains sub-populations each having a different half-life time to deterioration under UV radiation.

4. A composition according to claim 3, wherein the UV radiation is UV radiation from the sun.

5. A composition according to claim 3, wherein the walls of some of said microcapsule sub-populations have different thickness than the walls of others of the microcapsule sub-populations so that the microcapsules release their contained active agents at different times.

6. A composition according to claim 3, wherein the walls of some of said microcapsule sub-populations have chemical compositions that are different from the walls of others of the microcapsule sub-populations so that the microcapsules release their contents at different times.

7. A composition according to claim 3, wherein some of the microcapsule sub-populations have different diameters than others of the microcapsule sub-populations so that the microcapsules release their contents at different times.

8. A composition according to claim 1, wherein the walls of at least some of the microcapsules have two layers, at least one of the layers deteriorating when exposed to UV radiation.

9. A composition according to claim 8, wherein an inner layer of the microcapsules that have two layers is selected to deteriorate when exposed to UV radiation and an outer layer of the microcapsules that have two layers is soluble in a carrier of the active agent within the microcapsules that have two layers.

10. A composition according to claim 1, wherein the active agent is at least one sun blocking agent.

11. A composition according to claim 10, including some sun blocking agent in the medium.

12. A composition according to claim 10, wherein the sun blocking agent is organic.

13. A composition according to claim 12, wherein the sun blocking agent is selected from the group consisting of:

benzophenones; PABA; PABA derivatives; 2-ethylhexyl-para-diethylamino benzoate; cinnamates; salicylates; aminobenzoic acid ester; anthranilates; 2-ethylhexyl-2-cyano-3-diphenyl acrylate; 2-phenyl benzimidazole-5-sulfonic acid; aialloyl trioleate; 3-(4-methyl benzyledene) camphor; 4-isopropyl dibenzoyl methane; butyl methoxy dibenzoyl methane; 2-ethyl-2-cyano-3,3'diphenyl acrylate; 1-naphtyl-N-methyl carbamate; ascorbic acid; N-(hydroxymethyl)-N-(1,3-dihydroxymethyl-2,5-dioxo-4-imidazolidin yl-N'-hydroxymethyl urea; magnesium 1-hydroxy2(1H)-pyridinethione; N-(4-chlorophenyl)-N'-(3,4-dichlorophenyl) urea; and N-(1-chloro,2-methyl,3-beta-chloronaphtylether benzyl)-N'-chlorobenzoyl urea.

14. A composition according to claim 1, wherein the active agent is at least one of a fragrance, an antiperspirant, a dye, a cooling agent, a warming agent, a flavor, an insect repellent, an antibacterial agent, a hair conditioner, a hair coloring agent, a hair lightening agent or a self tanning agent.

15. A composition according to claim 1, wherein the medium includes at least one of: hydroxyethyl cellulose; hydroxypropyl cellulose; hydroxyethyl alkali metal carboxyalkyl cellulose derivatives; free acid hydroxyalkyl carboxyalkyl cellulose derivatives; polyvinyl alcohol; vinylpyrrolidone homopolymers and copolymers; polycarboxylic acid derivatives; polyacrylamides; vinyl ethyl ether homopolymers and copolymers; and ethylene oxide resins.

16. A composition according to claim 6, wherein the different half-life times of different microcapsule subpopulations is achieved by having the walls of each subpopulation comprise a different mixture of vinylpyrrolidone and alkylated vinylpyrrolidone, with shorter half-life times being associated with walls containing higher proportions of the alkylated vinylpyrrolidone.

17. A method of releasing a sun blocking agent onto a user's skin over time, the release rate being a function of exposure to UV radiation, the method comprising:

spreading a medium onto the skin of a user, the medium containing a multiplicity of microcapsules containing at least one sun blocking agent, said microcapsules having sufficient strength so that only a minority of the microcapsules rupture during application of the composition onto the user's skin;

providing a population of microcapsules with half-life times to deterioration under the influence of the UV radiation which is from about ½ hour to about 6 hours; and exposing the skin to the UV radiation to causing the microcapsules to deteriorate over time to release the at least one sun blocking agent onto the skin.

18. A method according to claim 17, wherein the half-life time of said microcapsules to deterioration under UV radiation is controlled by one or more of the following parameters:

microcapsule wall composition, microcapsule wall thickness and microcapsule diameter; and said sufficient strength is achieved by selecting microcapsules having a diameter not greater than 50 microns.

19. A method according to claim 18, wherein the population of microcapsules is provided as different subpopulations each having a different half-life time to deterioration under UV radiation.

20. A method according to claim 17, including exposing the skin to UV radiation from the sun.

21. A method according to claim 18, wherein said multiplicity of microcapsules contains different sub-populations each having a different half-life time to deterioration under UV radiation, walls of some of the microcapsule subpopulations being provided to have different thicknesses than the walls of others of the microcapsule sub-populations so that the microcapsules release their contained sun blocking agent at different times.

22. A method according to claim 18, wherein said multiplicity of microcapsules contains sub-populations each having a different half-life time to deterioration under UV radiation, the walls of some of the microcapsule subpopulations being provided with chemical compositions that are different from the walls of others of the microcapsule sub-populations so that the microcapsules release their contained sun blocking agents at different times.

23. A method according to claim 18, wherein said multiplicity of microcapsules contains sub-populations each having a different half-life time to deterioration under UV radiation, some of the microcapsule sub-populations have different diameters than others of the microcapsule subpopulations so that the microcapsules release their contained sun blocking agents at different times.

24. A method according to claim 18, wherein the walls of at least some of the microcapsules have two layers, at least one of the layers deteriorating when exposed to UV radiation.

25. A method according to claim 24, wherein an inner layer of the microcapsules that have two layers is provided to deteriorate when exposed to UV radiation and an outer layer of the microcapsules that have two layers is provided to be soluble in a carrier of the sun blocking agent within the microcapsules.

26. A method according to claim 17, including providing some sun blocking agent in the medium.

27. A method according to claim 17, wherein the sun blocking agent is organic.

28. A method according to claim 27, wherein the sun blocking agent is selected from the group consisting of:

benzophenones; PABA; PABA derivatives; 2-ethylhexyl-para-diethylamino benzoate; cinnamates; salicylates; aminobenzoic acid ester; anthranilates; 2-ethylhexyl-2-cyano-3-diphenyl acrylate; 2-phenyl benzimidazole-5-sulfonic acid; aialloyl trioleate; 3-(4-methyl benzyledene) camphor; 4-isopropyl dibenzoyl methane; butyl methoxy dibenzoyl methane; 2-ethyl-2-cyano-3,3'diphenyl acrylate; 1-naphtyl-N-methyl carbamate; ascorbic acid; N-(hydroxymethyl)-N-(1,3-dihydroxymethyl-2, 5-dioxo-4-imidazolidinyl-N'-hydroxymethyl urea; magnesium 1-hydroxy2(1H))-pyridinethione; N-(4-chlorophenyl)-N'-(3,4-dichlorophenyl) urea; and N-(1-chloro,2-methyl,3-beta-chloronaphtylether benzyl)-N'chlorobenzoyl urea.

29. A method according to claim 17, wherein the medium includes at least one of: hydroxyethyl cellulose; hydroxypropyl cellulose; hydroxyethyl alkali metal carboxyalkyl cellulose derivatives; free acid hydroxyalkyl carboxyalkyl cellulose derivatives; polyvinyl alcohol; vinylpyrrolidone homopolymers and copolymers; polycarboxylic acid derivatives; polyacrylamides; vinyl ethyl ether homopolymers and copolymers; and ethylene oxide resins.

30. A method according to claim 17, wherein the different half-life times of microcapsule sub-populations in the multiplicity of microcapsules is provided by providing the walls of each sub-population to comprise a different mixtures of vinylpyrrolidone and alkylated vinylpyrrolidone, wherein shorter half-life times are associated with a higher proportion of alkylated moeities.

31. A method of releasing an active agent onto the skin of a user over time, the release rate being a function of exposure to UV radiation, comprising:

spreading a medium onto the skin of a user, the medium containing a multiplicity of microcapsules containing at least one active agent, said microcapsules having sufficient strength so that only a minority of the microcapsules are ruptured during application of the composition onto the skin of a user;

providing a population of microcapsules with half-life times to deterioration under the influence of the UV radiation which is from about ½ to about 6 hours; and exposing the skin to the user to UV radiation to causing the microcapsules to deteriorate over time to release the at least one active agent onto the skin.

32. A method according to claim 31, wherein the half-life time of said microcapsules to deterioration under UV radiation is controlled by one or more of the following parameters:

microcapsule wall composition; microcapsule wall thickness and microcapsule diameter; and said sufficient strength is achieved by selecting microcapsules having a diameter not greater than 50 microns.

33. A method according to claim 32, wherein the multiplicity of microcapsules is provided as sub-populations of microcapsules each having a different half-life time to deterioration under UV radiation.

34. A method according to claim 32, including exposing the skin of a user to the UV radiation from the sun.

35. A method according to claim 32, wherein the walls of some microcapsule sub-populations of the multiplicity of microcapsules are provided to have different thickness than the walls of others of the microcapsule sub-populations so that the microcapsules release their contained active agent at different times.

36. A method according to claim 32, wherein the walls of some microcapsule sub-populations of the multiplicity of microcapsules are provided with chemical compositions that are different from the walls of others of the microcapsule sub-populations so that the microcapsules release their contained active agents at different times.

37. A method according to claim 32, wherein some microcapsule sub-populations of the multiplicity of microcapsules have different diameters than others of the microcapsule sub-populations so that the microcapsules release their contained active agents at different times.

38. A method according to claim 32, wherein the walls of at least some of the microcapsules have two layers, at least one of the layers deteriorating when exposed to UV radiation.

39. A method according to claim 38, wherein an inner layer of the microcapsules that have two layers is provided to be deteriorating when exposed to UV radiation and an outer layer of the microcapsules that have two layers is provided to be soluble in a carrier of the active agent within the microcapsules.

40. A method according to claim 32, wherein the active agent includes at least one of an antiperspirant, a dye, a cooling agent, a warming agent, a flavor, an insect repellent, an antibacterial agent, a hair conditioner, a self tanning agent, a hair coloring or lightening agent or a fragrance.

41. A method according to claim 32, wherein the different half-life times of microcapsule sub-populations of the multiplicity of microcapsules is provided by providing the walls of each sub-population to comprise different mixtures of vinylpyrrolidone and alkylated vinylpyrrolidone, wherein shorter half-life times are associated with a higher proportion of the alkylated vinylpyrrolidone.

* * * * *